US005924983A

United States Patent [19]

Takaki et al.

[11] Patent Number: 5,924,983

[45] Date of Patent: Jul. 20, 1999

[54] ELECTRICAL CONDUCTOR FOR BIOMEDICAL ELECTRODES AND BIOMEDICAL ELECTRODES PREPARED THEREFROM

[75] Inventors: Shunsuke Takaki; Masanao Shikano, both of Sagamihara, Japan

[73] Assignee: Minnesota Mining And Manufacturing Company, St. Paul, Minn.

[21] Appl. No.: 08/637,677

[22] PCT Filed: Apr. 29, 1996

[86] PCT No.: PCT/US96/05938

§ 371 Date: Apr. 26, 1996

§ 102(e) Date: Apr. 26, 1996

[87] PCT Pub. No.: WO97/41568

PCT Pub. Date: Nov. 6, 1997

Related U.S. Application Data

[51] Int. Cl.$^{6}$ ........ A61B 5/04

[52] U.S. Cl. ........ 600/372; 600/391; 600/392; 600/395; 600/396; 600/397; 607/152

[58] Field of Search ........ 128/639, 641, 128/643, 644; 607/152, 153; 600/372, 391, 392, 395, 396, 397

[56] References Cited

U.S. PATENT DOCUMENTS

| | | | |
|---|---|---|---|
| 3,976,055 | 8/1976 | Monter et al. | 128/2.06 E |
| 4,524,087 | 6/1985 | Engel | 427/2 |
| 4,539,996 | 9/1985 | Engel | 128/640 |
| 4,554,924 | 11/1985 | Engel | 128/640 |
| 4,715,382 | 12/1987 | Strand | 128/640 |
| 4,771,783 | 9/1988 | Roberts | 128/640 |
| 4,846,185 | 7/1989 | Carim | 128/641 |
| 4,848,348 | 7/1989 | Craighead | 128/639 |
| 4,848,353 | 7/1989 | Engel | 128/640 |
| 4,852,571 | 8/1989 | Gadsby et al. | 128/640 |
| 5,012,810 | 5/1991 | Strand et al. | 128/640 |
| 5,078,138 | 1/1992 | Strand et al. | 128/640 |
| 5,133,356 | 7/1992 | Bryan et al. | 128/640 |
| 5,215,087 | 6/1993 | Anderson et al. | 128/640 |
| 5,276,079 | 1/1994 | Duan et al. | 524/386 |
| 5,338,490 | 8/1994 | Dietz et al. | 252/500 |
| 5,352,315 | 10/1994 | Carrier et al. | 156/267 |
| 5,362,420 | 11/1994 | Itoh et al. | 252/500 |
| 5,385,679 | 1/1995 | Uy et al. | 252/500 |
| 5,505,200 | 4/1996 | Takaki | 128/640 |
| 5,571,165 | 11/1996 | Ferrari et al. | 607/152 |

FOREIGN PATENT DOCUMENTS

| | | | |
|---|---|---|---|
| 0 051 935 A2 | 5/1982 | European Pat. Off. | A61F 13/02 |
| 4-236940 | 8/1992 | Japan | A61B 5/0408 |
| 5-95922 | 4/1993 | Japan | A61B 5/0408 |
| WO 94/12585 | 6/1994 | WIPO | C09J 171/00 |

OTHER PUBLICATIONS

Brunauer, Emmett and Teller, J. Am. Chem. Soc., 60,309 (1938).

*Primary Examiner*—Jennifer Bahr
*Assistant Examiner*—David Ruddy
*Attorney, Agent, or Firm*—Gary L. Griswold; Walter N. Kirn; John H. Hornickel

[57] ABSTRACT

An electrical conductor and a biomedical electrode using the electrical conductor are disclosed. The electrical conductor has a flexible, non-conductive film and two different carbon-containing coatings on a major surface of the film. The electrical conductor coatings are a low porous carbon-containing coating and a high porous carbon-containing coating. The low porous carbon-containing coating contacts the film and the high porous carbon-containing coating contacts the low porous carbon-containing coating. A tab/pad style of biomedical electrode using the electrical conductor has a field of ionically conductive media containing electrolyte contacting the high porous carbon-containing coating. The electrolyte diffuses into the high porous carbon-containing coating for electrochemical advantages.

12 Claims, 1 Drawing Sheet

ELECTRICAL CONDUCTOR FOR BIOMEDICAL ELECTRODES AND BIOMEDICAL ELECTRODES PREPARED THEREFROM

FIELD OF THE INVENTION

This invention relates to electrically conductors for biomedical electrodes and biomedical electrodes prepared therefrom.

BACKGROUND OF THE INVENTION

Modern medicine uses many diagnostic procedures where electrical signals are received from a mammalian patient's body. Nonlimiting examples of diagnostic procedures include electrocardiograph (ECG or EKG) diagnosis or monitoring of electrical wave patterns of a mammalian heart. The point of contact between medical equipment used in these procedures and the skin of the patient is usually some sort of biomedical electrode. Such an electrode typically includes a conductor with a conductive medium adhered to or otherwise contacting skin of a patient.

For each diagnostic procedure, at least one biomedical electrode having an ionically-conductive medium containing an electrolyte is adhered to or otherwise contacts skin at a location of interest and also electrically connected to electrically diagnostic equipment. A component of the biomedical electrode is the electrical conductor in electrical communication with the ionically-conductive medium and the electrically diagnostic equipment.

Electrical conductors require excellent electrical conductivity and minimal electrical resistance for biomedical electrodes, especially when faint electrical signals are received from the patient. For this reason, metals or carbon are principally used. Among metals, silver is preferred because of its optimal conductivity. Biomedical electrodes which monitor a patient's conditions must be able to withstand the polarizing effects of a defibrillation procedure for a heart. So, a polarizable biomedical electrode with carbon or graphite conductor as shown in Japanese unexamined patent publication No. 4-236940 is not suitable for the application of the defibrillation. For this reason, silver chloride is preferably used with a silver conductor to create a depolarizing electrical conductor in biomedical electrodes.

The typical electrical conductor containing silver/silver chloride(Ag/AgCl) includes the Ag/AgCl eyelet which is electroplated with silver and converted the surface of silver (Ag) layer to silver chloride (AgCl). Recently, disposable, thin and flexible electrodes with thin and flexible conductor sheet which is formed by coating with Ag/AgCl ink on the thin and flexible plastic film was developed as shown in U.S. Pat. No. 5,078,138(Strand et al.). There is a principal difficulty with a biomedical electrode containing Ag/AgCl conductor. The cost of electrodes containing Ag/AgCl conductor has been greater than desired for a disposable electrode device.

In order to reduce the amount of Ag/AgCl used in biomedical electrodes, two kinds of solutions have been attempted. One was to use a conductor containing inexpensive graphite, carbon or other galvanically inactive materials in association with Ag/AgCl, such as those electrodes disclosed in U.S. Pat. No. 3,976,055 (Monter et al.). However, the electrode was still expensive due to the presence of Ag/AgCl particles that had to be located on the surface of conductor in order to keep good electrical performance.

Another attempt was to form Ag/AgCl layer on inexpensive graphite layer, carbon layer or other galvanically inactive material, such as that disclosed in U.S. Pat. No. 4,852,571 (Gadsby et al.) or Japanese unexamined patent publication No. 5-95922 (Sakagawa). However, the manufacturing cost was greater for these dual layer conductors than the cost for a single layered conductor, because the dual layered conductor had to be coated with two kinds of materials. Further, a significant amount of Ag/AgCl was used in the conductor to achieve good electrical performance.

SUMMARY OF THE INVENTION

The present invention solves unresolved problems in the prior art by providing an inexpensive, but electrically superior electrical conductor, especially for biomedical electrodes and a biomedical electrode using such electrical conductor.

One aspect of the present invention provides an electrical conductor, comprising a flexible, non-conductive film and carbon-containing coatings on a major surface of the film.

The electrical conductor comprises two different carbon-containing coatings in a sequentially manufactured relationship. While the two different carbon-containing coatings are different, many of the ingredients for both coatings are alike and are employed in similar weight percents. Thus, while two distinct coatings are contemplated for use in the electrical conductor of the present invention, the two coatings can be considered two portions of a single layer of electrically conductive carbon-containing material. In this manner, the electrical conductor of the present invention is different from those prior art conductors having two specific layers of galvanically different compositions such as Gadsby et al. Unlike Gadsby et al., the electrically conductive material of the present invention does not require one layer to be free of a carbon-containing composition.

The two carbon-containing coatings have distinctly different purposes in the electrical conductor of the present invention.

One carbon-containing coating, the coating contacting the flexible, non-conductive film, comprises a low porous, conductive coating comprising carbon powder and hydrophobic polymer serving as a binder in the low porous carbon-containing coating when in contact with the flexible, non-conductive film, optionally silver-containing powder, and optionally crosslinking agent.

The second carbon-containing coating, the coating contacting the ionically conductive medium containing electrolyte, comprises a high porous conductive coating comprising silver-containing powder, carbon powder, a hydrophobic or hydrophilic polymer serving as a binder in the high porous carbon-containing coating when in contact with the low porous carbon-containing coating, and optionally a crosslinking agent.

For purposes of this invention, "high porous" means sufficient porosity to permit an electrolyte from the ionically conductive medium to diffuse into the carbon-containing coating contacting the ionically conductive medium. Preferably, one manner of measuring whether a coating is "high porous" can be based on a test method published by Brunauer, Emmett and Teller in J. Am. Chem. Soc., 60,309 (1938) ("BET Method") whereby the high porous carbon-containing coating has an $N_2$ adsorbing surface area of more than about 8 $m^2/m^2$ of unit area.

For purposes of this invention, "low porous" means such limited porosity to minimize water absorbency and minimize degradation of electrical conductivity caused by interference of charge transfer from the high porous carbon-containing coating to the low porous carbon-containing coating. Preferably, one manner of measuring whether a coating is "low porous" can be based on the BET Method whereby the low porous carbon-containing coating has an $N_2$ adsorbing surface area of less than about 5 $m^2/m^2$ of unit area.

Thus, electrical conductors of the present invention combine a high porous carbon-containing coating with a low porous carbon-containing coating, with the high porous carbon-containing coating being contact with an ionically conductive medium containing an electrolyte.

For purposes of this invention, a "hydrophobic polymer serving as a binder" in the low porous carbon-containing coating means a hydrophobic polymer has minimal or little water absorbency in order to minimize degradation of the electrical conductivity caused by interference of charge transfer in the low porous carbon-containing coating.

Another aspect of the present invention is a method for manufacturing an electrical conductor, comprising the step of tandemly coating a major surface of a flexible, non-conductive film with two different formulations of ink, one ink forming a low porous carbon-containing coating on the major surface of the film and the second ink forming a high porous carbon-containing coating on the low porous carbon-containing coating.

Another aspect of the present invention a biomedical electrode, comprising an electrical conductor of the present invention and an ionically conductive medium containing an electrolyte in contact with the low porous carbon-containing coating of the electrical conductor.

A feature of the present invention is that each carbon-containing coating of the electrical conductor serves a distinctly different purpose based on the ingredients chosen for the coating.

Another feature of the present invention is that the electrical conductor and the biomedical electrode can be made quite inexpensively from larger quantities of inexpensive ingredients and smaller quantities of more expensive ingredients.

An advantage of the present invention is that the electrical conductor and the biomedical electrode using the electrical conductor perform excellently.

Further features and advantages can be found in a discussion of embodiments of the invention in relation to the following drawings.

BRIEF DESCRIPTION OF THE DRAWINGS

FIG. 1(*b*) is a cross section one embodiment of an electrical conductor of the present invention which a tab area is not covered with top conductive layer.

EMBODIMENTS OF THE INVENTION

Figure 1A:
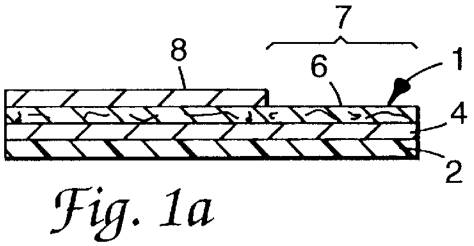
FIG. 1(*a*) is a cross section of one embodiment of an electrical conductor of the present invention, which a tab area is covered with top conductive layer.
Figure 1B:
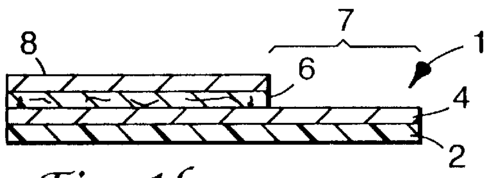

FIG. 1 illustrates a cross sectional view of an electrical conductor 1 of the present invention having a film 2 contacting a low porous carbon-containing coating 4, which in turn is contacting a high porous carbon-containing coating 6. FIG. 1(*a*) is a type which a tab area 7 without field 8 of conductive adhesive is covered with a high porous carbon-containing coating. FIG. 1 (*b*) is a type which a tab area 7 is not covered with a high porous carbon-containing coating. The thickness of the high porous carbon-containing coating 6 and the low porous carbon-containing coating 4 affect the performance and cost of conductor 1. Thinner layers attain lower cost for manufacturing, but easily could cause poor electrical and mechanical performance. So it is preferable to adopt an optimal thickness of coatings 4 and 6 together to satisfy both requirements. For the electrical conductor 1, the thickness of the flexible, non-conductive film 2 can be from about 10 μm to about 200 μm, the thickness of the low porous carbon-containing coating 4 can be from about 1 to about 20 μm, and the thickness of the high porous carbon-containing coating 6 can be from about 10 to about 20 μm.

Flexible, Non-Conductive Film

The film 2 is a backing sheet serving to both mechanically protect the biomedical electrode during storage and use and to electrically insulate the electrical conductor during use.

Film 2 can have a thickness ranging from about from about 10 μm to about 200 μm, and preferably from about 50 μm to about 100 μm.

The shape of film 2 can ultimately be the shape of a tab/pad style biomedical electrode and thus can have dimensions varying according to the geometry of the biomedical electrode desired. Thus, film 2 can have a length ranging from about 0.5 cm to about 10 cm and preferably from about 1 cm to about 5 cm. Film 2 can have a width ranging from about 0.5 cm to about 10 cm and preferably from about 1 cm to about 5 cm.

Nonlimiting examples of flexible, non-conductive materials suitable for use as film 2 are polyester, poly(ethylene), poly(propylene), poly(vinyl chloride), and the like. Of these materials, commercially available polyester film of 75 μm thickness is presently preferred.

Low Porous Carbon-containing Coating

Low porous carbon-containing coating 4 contacts film 2 on a major surface thereof and provides an underlying electrical conductivity for conductor 1.

The low porous carbon-containing coating 4 comprises carbon powder and hydrophobic polymer serving as a binder for the low porous carbon-containing coating when contacting the flexible and non-conductive film 2, and optionally, silver-containing powder.

As stated above, the low porous carbon-containing coating 4 can have an $N_2$ adsorbing surface area per unit area of less than about 5 $m^2/m^2$ as measured by the BET Method described above. More desirably, the low porous carbon-containing coating 4 can have an $N_2$ adsorbing surface area per unit area of from about 2 $m^2/m^2$ to about 5 $m^2/m^2$. Most desirably, the low porous carbon-containing coating can have an $N_2$ adsorbing surface area per unit area of from about 3 $m^2/m^2$ to about 4 $m^2/m^2$. Increasingly within these ranges, the low porous carbon-containing coating has little or no porosity and little or no water absorbency. Thus degradation that causes interference of charge transfer can be inhibited. As a result, good electrical conductivity can be easily maintained for a long time.

Carbon powder for the low porous carbon-containing coating 4 can be graphite powder, carbon black powder, or combinations thereof The total content of the carbon powder in the low porous carbon-containing coating 4 can range from about 10 weight percent to about 70 weight percent of the total low porous carbon-containing coating and preferably is from about 40 weight percent to about 50 weight percent.

Average adsorbing area for carbon powder in coating 4 is one manner to characterize useful carbon powder for the present invention because the electrolyte diffuses through the micro pores of carbon particles and spaces between carbon particles. Suitably, the average adsorbing surface area of graphite powder and/or carbon black powder used in coating 4 is less than about 400 $m^2/g$, more desirably less than about 350 $m^2/g$, most desirably less than about 250 $m^2/g$, as measured by the BET Method described above. The lower limit of the average adsorbing surface area of the carbon powder is preferably about 30 $m^2/g$.

Nonlimiting examples of conductive carbon powder are "S-CP graphite" brand powder from Nippon Kokuen Ind. in Shiga, Japan, #3050B brand powder from Mitsubishi Chem. in Tokyo, Japan, and "Ketjen Black EC" brand powder from Akzo Chem. Co. of the Netherlands.

A suitable hydrophobic polymer to serve as a binder in the low porous carbon-containing coating is a polymer having a glass transition temperature (Tg) of less than 0° C. Nonlimiting examples of hydrophobic polymers serving as a binder are polyurethane, polyester, polyvinylchloride, acrylic resin, polyvinylacetate, and combinations thereof. A commercially available binder is "ESTANE 5703 polyurethane pellets" of Union Carbide Co. in USA.

The total content of the hydrophobic polymer in the low porous carbon-containing coating 4 can range from about 30 weight percent to about 90 weight percent, and preferably from about 40 weight percent to about 60 weight percent.

Optionally, coating 4 can contain silver-containing powder. Silver-containing powder useful in low porous carbon-containing coating 4 can comprise silver, silver halide (particularly silver chloride), or combinations of both.

The total content of silver-containing powder in the low porous carbon-containing coating 4 can range from 0 to about 12 weight percent of the low porous carbon-containing coating, desirably from 0 to about 6 weight percent and preferably about 3 weight percent. The ratio of Ag and AgCl in a Ag/AgCl ink can range from about 90:10 to about 50:50. Preferably, a ratio of about 90:10 is used. Nonlimiting examples of commercially available Ag ink or Ag/AgCl ink are "Electrodac 461SS Ag ink" of Achson Inc. in U.S.A, "R-301 Ag/AgCl ink" of ERCON Inc. of Waltham Mass. in USA, "DB 92343 Ag/AgCl ink" of Acheson Inc. of Michigan in USA.

Optionally, coating 4 can employ a crosslinking agent to assist in adherence of coating 4 on film 2. The amount of crosslinking agent added can range from about 0.1 weight percent to about 20 weight percent of the solvent based ink. Preferably, 0.3 to 3 weight percent of the crosslinking agent is added for the solvent based ink. The crosslinking agent can be a polyisocyanate (such as polymeric diphenyl Methane Di Isocyanate or polyisocyanurate. Nonlimiting examples of crosslinking agent are "PAPI 135" polyisocyanate of Dow Mitsubishi Kasei Co. in Japan and "Takenate D-204" polyisocyanurate of Takeda Chem. Ind. in Japan.

The thickness of the low porous carbon-containing coating can range from about 1 μm to about 20 μm, and more desirably from about 5 μm to about 15 μm. The thickness of the low porous carbon-containing coating can be unexpectedly thinner than carbon-containing coatings known in the art.

Previously in the art, when graphite ink was used to produce an electrical conductor having a thickness of less about 5 μm, the electrical conductivity of the coating decreased while the alternating current impedance of the electrode unacceptably increased. Prior art graphite electrical conductors generally needed a thickness of at least 10 μm in order to achieve a suitable electrical conductivity.

However, a low porous carbon-containing coating 4 of the present invention can have a thickness less than about 5 μm while retaining a high electrical conductivity and a low alternating current impedance because coating 4 also contains the silver-containing powder therein. Even though silver-containing powder is an expensive additive to the coating 4, the material cost of a 5 μm thick coating 4 of the present invention is less expensive than a 10 μm layer of graphite ink, because the coated weight of the coating 4 is 50% of the coated weight of the conventional graphite ink at its required thickness.

High Porous Carbon-containing Coating

High porous carbon-containing coating 6 contacts low porous carbon-containing coating 4 and provides the interface between electrical conductor 1 and ionically conductive media containing electrolyte in a biomedical electrode.

The high porous carbon-containing coating 6 comprises silver-containing powder, carbon powder, and a hydrophobic or hydrophilic polymer serving as a binder for the high porous carbon-containing coating when contacting the low porous carbon-containing coating 4.

As stated above, the high porous carbon-containing coating 6 can have an $N_2$ adsorbing surface area per unit area of greater than about 8 $m^2/m^2$ as measured by the BET Method described above. More desirably, the high porous carbon-containing coating 6 can have an $N_2$ adsorbing surface area per unit area of greater than about 10 $m^2/m^2$. Most desirably, the high porous carbon-containing coating can have an $N_2$ adsorbing surface area per unit area of greater than about 40 $m^2/m^2$. The practical upper limit in the current technology is about 200 $m^2/m^2$, but the present invention contemplates exceeding that limit if the technology otherwise advances.

Increasingly within these threshholds, the high porous carbon-containing coating, electrolyte from ionically conductive media in a biomedical electrode can diffuse into coating 6. This diffusion provides the unexpected advantage of improving the interface between the ionically conductive media and the electrically conductive conductor 1 in a biomedical electrode. Further when silver-containing powder is present in coating 6 as a mixture of silver and silver halide, the silver-containing powder can react with the electrolyte in coating 6 to further the electrochemical advantage of depolarization for a biomedical electrode. With this possible reaction, the amount of silver-containing powder can be reduced, further minimizing cost of the conductor while improving electrical performance.

Average adsorbing area for carbon powder in coating 6 is one manner to characterize useful carbon powder for the present invention because the electrolyte diffuses through micro pores of carbon particles and spaces between carbon particles. Suitably, the average adsorbing surface area of graphite powder and/or carbon black powder used in coating 6 is greater than about 600 $m^2/g$, more desirably greater than about 800 $m^2/g$, most desirably greater than about 900 $m^2/g$, as measured by the BET Method described above. The upper limit of the average adsorbing surface area of the carbon powder is preferably about 1500 $m^2/g$.

In order to inhibit degradation caused by interference of charge transfer, the low porous carbon-containing coating 4 having little or no porosity and little or no water absorbency is employed between flexible, non-conductive film 2 and the high porous carbon-containing coating 6 having a porous structure. Because electrolyte diffused into coating 6 can not diffuse into the low porous carbon-containing coating 4, good electrical conductivity in conductor 1 can be maintained.

Silver-containing powder useful in high porous carbon-containing coating 6 can comprise silver, silver halide (particularly silver chloride), or combinations of both.

Average diameter of the silver-containing powder can be one manner to characterize useful silver-containing powder for coating 6. The average diameter of Ag powder or AgX powder (particularly AgCl powder) is desirably from about 0.5 to 30 μm and more desirably from about 1 to 20 μm. By using silver-containing powder with diameters of these ranges, a high porous structure can be easily made in the coating 6, and electrolyte from the ionically conductive media can easily diffuse into coating 6. Excellent electrochemical performance in coating 6 results.

The total content of silver-containing powder in the high porous carbon-containing coating 4 can range from 1 to about 50 weight percent of the high porous carbon-containing coating, desirably from about 6 to about 30 weight percent and preferably from about 10 weight percent to about 25 weight percent.

The ratio of Ag and AgCl in a Ag/AgCl ink can range from about 90:10 to about 50:50. Preferably, a ratio of about 90:10 is used. Nonlimiting examples of commercially available Ag ink or Ag/AgCl ink are "Electrode 461SS Ag ink" of Achson Inc. in USA, "R-301 Ag/AgCl ink" of ERCON Inc. of Waltham Mass. in USA, "DB 92343 Ag/AgCl ink" of Acheson Inc. of Michigan in USA.

Carbon powder for the high porous carbon-containing coating 6 can be graphite powder, carbon black powder, or combinations thereof and can be selected from the same sources as used for coating 4.

The total content of the carbon powder in the high porous carbon-containing coating 4 can range from about 10 weight percent to about 80 weight percent and preferably is from about 30 weight percent to about 40 weight percent.

Unlike the kind of the hydrophobic polymer for serving as the binder in the low porous carbon-containing coating 4, the polymer for serving as the binder for the high porous carbon-containing coating 6 is not limited. Any of the hydrophobic polymers mentioned above are also useful as a binder for coating 6 whether prepared from solutions or emulsions provided that some diffusion of electrolyte into coating 6 is possible.

In addition, nonlimiting examples of useful hydrophilic polymers include water soluble or dispersible polymers (such as poly(vinyl pyrrolidone), poly(vinyl alcohol), or polymers made from macromonomers or microgels), and natural-occurring or synthetically modified naturally occurring polymers (such as celluloses). Preferably, hydrophilic polymer is used as the binder, especially methylcellulose to provide excellent diffusion of electrolyte into high porous carbon-containing coating 6.

The total content of the polymer in the high porous carbon-containing coating 6 can range from about 20 weight percent to about 90 weight percent, preferably from about 55 weight percent to about 75 weight percent, and most preferably from about 60 weight percent to about 70 weight percent.

Optionally, coating 6 can also employ a crosslinking agent to assist in adherence of coating 6 on coating 4. The amount of crosslinking agent added can range from about 0.1 weight percent to about 20 weight percent for the solvent based ink. Preferably, 0.3 to 3 weight percent of the crosslinking agent is added for the solvent based ink. The crosslinking agent can be a polyisocyanate (such as polymeric or polyisocyanurate). Nonlimiting examples of crosslinking agent are "PAPI 135" polyisocyanate of Dow Mitsubishi Kasei Co. in Japan and "Takenate D-204" polyisocyanurate of Takeda Chem. Ind. in Japan.

The thickness of the high porous carbon-containing coating 6 can be from about 1 μm to about 20 μm, and preferably from about 4 μm to about 15 μm. The lower limit of the thickness of the coating 6 is determined by the amount of silver-containing powder present. The greater the amount of silver-containing powder in coating 6, the thinner coating 6 can be.

For example, when the silver-containing powder is made from a Ag/AgCl ink and comprises 19 weight percent of coating 6, a thickness of 5 μm is sufficient to achieve required electrical conductivity performance.

Method of Making Electrical Conductors

The low porous carbon-containing coating 4 is made by applying an ink on to a major surface of film 2. The techniques of applying inks for biomedical electrodes are well known to those skilled in the art and need not be repeated here. Preferably, a die coating technique is used to apply composition 14 on to film 2.

The high porous carbon-containing composition 16 is made by applying an ink on to coating 4. The techniques of applying inks for biomedical electrodes are well known to those skilled in the art and need not be repeated here. Preferably, a die coating technique is used to apply coating 6 on to coating 4.

The ink for high porous carbon-containing coating 6 can be a blend of a variety of silver-containing inks and carbon-containing inks. The total solid content of the silver containing ink in a blended ink for the high porous carbon-containing coating from about 1 to about 50 weight percent, and more desirably from about 20 to about 40 weight percent for the total solid ink. Preferably the silver containing ink is a Ag/AgCl ink.

The porosity and the water absorbency of the high porous carbon-containing coating 6 and low porous carbon-containing coating 4 are respectively controlled by the materials and formulation of coating inks, dispersibility of carbon particles and the drying temperature during manufacturing.

The method for manufacturing conductor 1 comprises a step of tandemly coating a flexible, non-conductive film 2 with two kinds of ink, the first ink for low porous carbon-containing coating 4, and the second ink for high porous carbon-containing coating 6.

Ink for coating 4 can comprise a graphite ink and/or a carbon ink or, if silver-containing powders are desired, a blended ink of a mixture of a graphite ink and/or a carbon ink and an Ag/AgCl ink and/or an Ag ink.

Ink for coating 6 can comprise comprises a blended ink of a mixture of a carbon ink for high conductivity and/or a graphite ink for high conductivity and an Ag/AgCl ink.

The graphite ink or the carbon ink in the blended ink for the low porous carbon-containing coating 4 can be a solvent-based ink or water-based ink comprising conductive carbon powder, hydrophobic polymer binder and solvents. The carbon powder can have a grain size of about 30 nm to 30 μm with a low absorbing surface area of desirably less than about 400 $m^2/g$ measured by the BET Method. Because of the grain size of the powder and the number of grain gaps in the coated coating 4 are small, coating 4 is less porous.

For the solvent of the composition of coating 4, a mixture of a high boiling point solvent (i.e., over 150° C.) and a low boiling point solvent (i.e., less than 150° C.) is used. The high boiling point solvent is added to inhibit flash evaporation of solvents under the high temperature for drying of over 150° C. in the short ovens. The ratio of the high boiling point solvent and the low boiling point solvent can range from about 0:100 to about 50:50. Preferably, the ratio ranges from about 0:100 to about 25:75 is used for drying at the high temperature of over 150° C.

The temperature used for drying the composition to form coating 4 needs to be lower than the highest boiling point of solvents used, in order not to form a porous structure in coating 4.

The solvent with a low boiling point can be selected from methyl ethyl ketone, toluene, propylene glycol mono methyl ether acetate, methyl propyl ketone and the like. The solvent with a high boiling point can be selected from buthyl carbitol acetate (diethylene glycol mono buthyl ether acetate), diethylene glycol mono buthyl ether, cyclohexanone and the like. The content of solvents ranges from about 20 weight percent to about 90 weight percent for the ink for coating 4. Preferably, the solvents range from about 60 weight percent to about 90 weight percent for the ink used for coating 4.

The ink for the low porous carbon-containing coating 4 can be prepared using a disperser such as a sand mill, an attritor, or a paint mill after mixing with all raw materials by a high shear mixer.

The ink for high porous carbon-containing coating 6 can be prepared using the same mixing and dispersing equipment, using the same solvents, and the same application technique as for coating 4, except that the drying temperature used should be higher than the highest boiling point of solvents used in order to form a porous structure in coating 6 by flash evaporation of solvent.

One coating method useful in the present invention employs a single pass of film 2 through a first coater that applies ink and dries ink in a first oven to form coating 4 and then through a second coater that applies ink and dries ink in a second oven to form coating 6. This "tandem" or sequential coating method is preferred over simultaneously coating techniques. For any portion of film that is not be coated, a strip coating method can be used according to techniques known to those skilled in the art.

Biomedical Electrodes

Biomedical electrodes employing electrical conductors of the present invention are useful for diagnostic (including monitoring) and therapeutic purposes. In its most basic form, a biomedical electrode comprises an ionically conductive medium contacting mammalian skin and a means for electrical communication, the electrical conductors of the present invention, interacting between the conductive medium and electrical diagnostic, therapeutic, or electrosurgical equipment.

Figure 2:
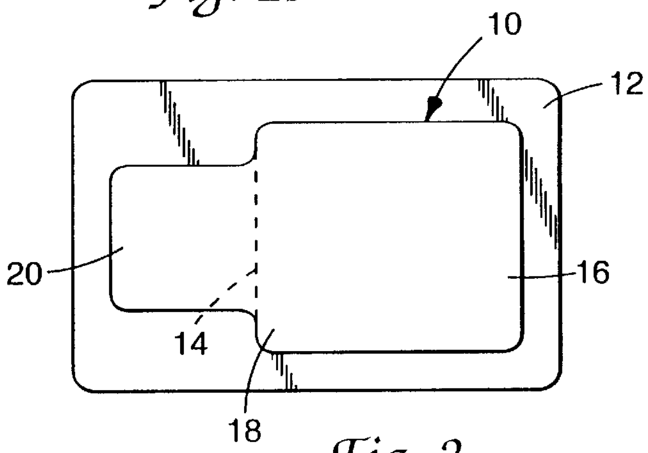
FIG. 2 is a top plan view of a biomedical electrode containing an adhesive composition of the present invention, used for diagnosis or monitoring of heart conditions of a mammalian patient.
Figure 3:
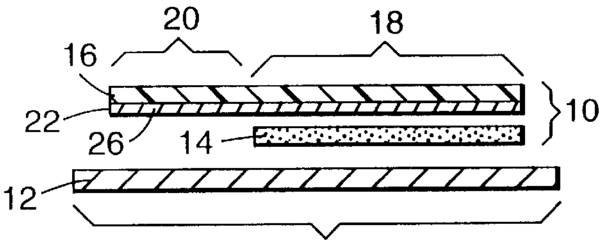
FIG. 3 is a cross-sectional view of the biomedical electrode of FIG. 2.

FIGS. 2 and 3 show either a disposable diagnostic electrocardiogram (ECG or EKG) or a transcutaneous electrical nerve stimulation (TENS) electrode on a release liner 12. Electrode 10 includes a field 14 of ionically conductive media having an electrolyte, preferably a biocompatible and adhesive conductive medium, for contacting mammalian skin of a patient upon removal of protective release liner 12. Electrode 10 includes means for electrical communication 16 comprising a conductor member of the present invention having a conductive interface portion 18 contacting field 14 of conductive medium and a tab portion 20 extending beyond field 14 of conductive medium for mechanical and electrical contact with electrical instrumentation (not shown). Means 16 for electrical communication includes a conductive layer 26 coated on at least the side 22 contacting field 14 of conductive medium.

To enhance mechanical contact between an electrode clip (not shown) and conductor member 16, an adhesively-backed polyethylene tape can be applied to tab portion 20 on the side opposite side 22 having the dual conductive coating 26. A surgical tape commercially available from 3M Company as "Blenderm" tape can be employed for this purpose.

Nonlimiting examples of biomedical electrodes which can use electrical conductors of the present invention include electrodes disclosed in U.S. Pat. Nos. 4,524,087; 4,539,996; 4,554,924; 4,848,353 (all Engel); 4,846,185 (Carim); 4,771,783 (Roberts); 4,715,382 (Strand); 5,012,810 (Strand et al.); and 5,133,356 (Bryan et al.), the disclosures of which are incorporated by reference herein.

In some instances, the means for electrical communication can be an electrically conductive tab extending from the periphery of the biomedical electrodes such as that seen in U.S. Pat. No. 4,848,353 or can be a conductor member extending through a slit or seam in an insulating backing member, such as that seen in U.S. Pat. No. 5,012,810.

Another type of diagnostic procedure which can employ a biomedical electrode of the present invention is the longer term monitoring of electrical wave patterns of the heart of a patient to detect patterns of abnormality. A preferred biomedical electrode structure is disclosed in U.S. Pat. No. 5,012,810 (Strand et al.) which is incorporated by reference.

Figure 4:
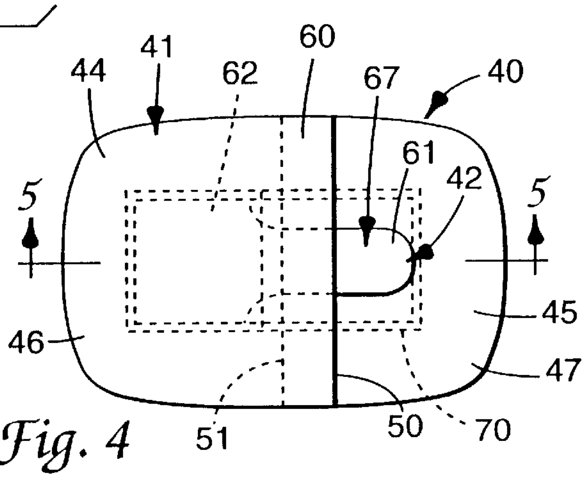
FIG. 4 is top plan view of a monitoring biomedical electrode containing an adhesive composition of the present invention, used for longer term diagnosis or monitoring of heart conditions.
Figure 5:
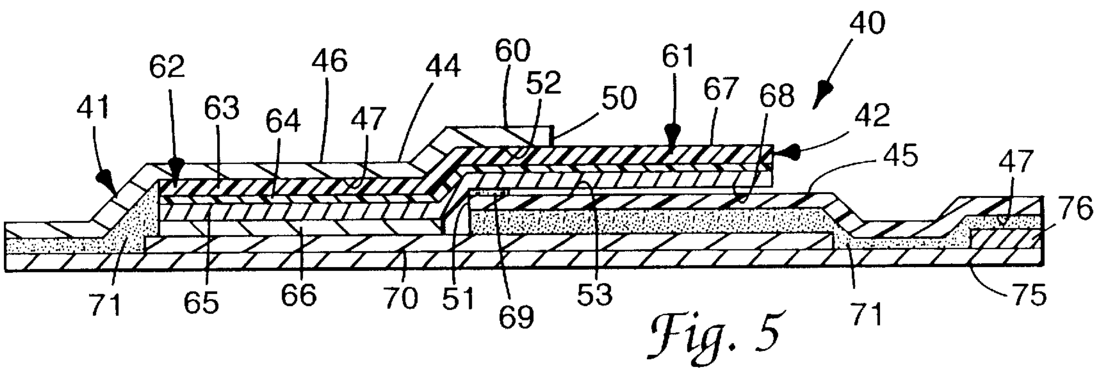
FIG. 5 is a cross-sectional view of the monitoring biomedical electrode of FIG. 4.

FIGS. 4 and 5 substantially correspond to FIGS. 2 and 3, respectively, of U.S. Pat. No. 5,012,810. Electrode 40 includes an insulator construction 41, and a conductor member 42.

The insulator construction 41 includes first and second sections 44 and 45 which, together, define opposite sides 46 and 47 of the insulator construction 41. As seen in FIG. 4, each section 44 and 45 includes an elongate edge portion 50 and 51, respectively. The edge portions 50 and 51 each include a border portion 52 and 53, respectively, which comprise a peripheral portion of each section 44 and 45, respectively, and extending along edges 50 and 51, respectively. In that manner, sections 44 and 45 are oriented to extend substantially parallel to one another, with edge portions 50 and 51 overlapping one another such that border portions 52 and 53 overlap. A seam 60 is created between edge portions 50 and 51. "Substantially parallel" does not mean that the sections 44 and 45 are necessarily precisely parallel. They may be out of precise coplanar alignment due, for example, to the thickness of the conductor member 42.

Conductor member 42 is substantially similar to biomedical electrical conductor 16 described above, having a tab portion 61 corresponding to tab portion 20 described above and a pad portion 62 corresponding to conductive interface portion 18 described above. Like biomedical electrical conductor member 16, conductor member 42 can be any of the embodiments disclosed above. Optionally, an adhesively-backed polyethylene tape can be applied to tab portion 61 in the same manner as that for the embodiment of FIGS. 2 and 3 in order to enhance mechanical contact.

In general, electrode 40 is constructed such that tab portion 61 of conductor member 42 projects through seam 60 and over a portion of surface or side 46. As a result, as seen in FIGS. 4 and 5 pad portion 62 of conductor member 42 is positioned on one side 46 of insulator construction 41, and the tab portion 61 of conductor member 42 is positioned on an opposite side 46 of insulator construction 41. It will be understood that except where tab portion 61 extends through seam 60, the seam may be sealed by means of an adhesive or the like.

As seen in FIG. 5, lower surface 68 of tab portion 61 is shown adhered in position to section 45, by means of double-stick tape strip 69. That is, adhesion in FIG. 5 between the tab portion 61 and section 45 is by means of adhesive 69 underneath tab portion 61.

In FIG. 5, a field 70 of conductive adhesive of the present invention is shown positioned generally underneath conductive member 42. Optionally, field 70 of conductive adhesive will be surrounded by a field 71 of biocompatible skin adhesive also applied to insulator construction 41 the side thereof having pad portion 62 thereon.

In FIG. 5, a layer of release liner 75 is shown positioned against that side of electrode 40 which has optional skin adhesive 71, conductive adhesive 70 and pad portion 62 thereon. Optionally as shown in FIG. 5, a spacer 76 or tab 76 can be positioned between release liner 75 and a portion of insulator construction 41, to facilitate the separation.

A variety of release liners 75 may be utilized; for example, a liner comprising a polymer such as a polyester or polypropylene material, coated with a silicone release type coating which is readily separable from the skin adhesive and conductive adhesive.

A variety of materials may be utilized to form the sections 44 and 45 of the insulator construction 41. In general, a flexible material is preferred which will be comfortable to the user, and is relatively strong and thin. Preferred materials are polymer foams, especially polyethylene foams, non-woven pads, especially polyester non-wovens, various types of paper, and transparent films. Nonlimiting examples of transparent films include polyester film such as a "Melinex" polyester film commercially available from ICI Americas, Hopewell, Va. having a thickness of 0.05 mm and a surgical tape commercially available from 3M Company as "Transpore" unembossed tape.

The most preferred materials are non-woven pads made from melt blown polyurethane fiber, which exhibit exceptional flexibility, stretch recovery and breathability. Melt blown polyurethane materials usable in insulator construction 41 in electrodes according to the present invention are generally described in European Patent Publication 0 341 875 (Meyer) and corresponding U.S. Pat. No. 5,230,701 (Meyer et al.), incorporated herein by reference.

Optionally the insulator construction has a skin adhesive on its surface contacting the remainder of the electrode 40.

Preferred web materials (melt blown polyurethanes) for use in insulator construction 41 have a web basis weight of about 60–140 g/m$^2$ (preferably about 120 g/m$^2$). Such materials have an appropriate tensile strength and moisture vapor transmission rate. A preferred moisture vapor transmission rate is about 500–3000 grams water/m$^2$/24 hours (preferably 500–1500 grams water/m$^2$/24 hours) when tested according to ASTM E96-80 at 21° C. and 50% relative humidity. An advantage to such materials is that webs formed from them can be made which exhibit good elasticity and stretch recovery. This means that the electrode can stretch well, in all directions, with movement of the subject, without loss of electrode integrity and/or failure of the seal provided by the skin adhesive. Material with a stretch recovery of at least about 85%, in all directions, after stretch of 50% is preferred.

It will be understood that a variety of dimensions may be utilized for the biomedical electrode disclosed herein. Generally an insulator construction of about 3.5–4.5 cm by 5.5–10 cm will be quite suitable for typical foreseen applications.

Nonlimiting examples of ionically conductive media useful as field 14 in electrode 10 or as field 70 in electrode 40 include those ionically conductive compositions disclosed in U.S. Pat. Nos. 4,524,087 (Engel), 4,539,996 (Engel), 4,848,353 (Engel); 4,846,185 (Carim); 5,225,473 (Duan); 5,276,079 (Duan et al.); 5,338,490 (Dietz et al.); 5,362,420 (Itoh et al.); 5,385,679 (Uy et al.); copending, coassigned applications PCT Publication Nos. WO 95/20634 and WO 94/12585 and copending coassigned U.S. patent application Ser. Nos. US95/17079 (Attorney Docket No. 51537PCT4A), US95/16993 (Attorney Docket No. 51290PCT8A); and US 95/16996 (Attorney Docket No. 48381PCT1A), the disclosures of which are incorporated by reference herein.

Thickness of the ionically conductive medium field 16 can range from about 0.25 mm to about 2.5 mm and preferably 0.63 mm in order to maintain a low profile, multi-layer biomedical electrode construction.

It will also be understood that a variety of materials may be utilized as the skin adhesive. Typically, acrylate ester adhesives will be preferred. Acrylate ester copolymer adhesives are particularly preferred. Such material are generally described in U.S. Pat. Nos. 2,973,826; Re 24,906; Re 33,353; 3,389,827; 4,112,213; 4,310,509; 4,323,557; 4,732,808; 4,917,928; 4,917,929; and European Patent Publication 0 051 935, all incorporated herein by reference.

In particular, an adhesive copolymer having from about 95 to about 97 weight percent isooctyl acrylate and from about 5 to about 3 percent acrylamide and having an inherent viscosity of 1.1–1.25 dl/g is presently preferred.

Adhesive useful for adhesive 69 can be any of the acrylate ester adhesives described above in double stick tape form. A presently preferred adhesive is the same adhesive as presently preferred for the skin adhesive except having an inherent viscosity of about 1.3–1.45 dl/g.

It will be understood that the dimensions of the various layers, and their conformation during association, are shown somewhat exaggerated in FIG. 5, to facilitate an understanding of the construction. In general, an overall substantially flat appearance with only a very minor "s" type bend in the conductive member 42 is accommodated by the arrangement, despite the multi-layered construction of member 42.

When used for diagnostic EKG procedures, electrodes shown in FIGS. 2 and 3 or those electrodes shown in U.S. Pat. No. 4,539,996 are preferred. When used for monitoring electrocardiogram (ECG) procedures, electrodes shown in FIGS. 4 and 5 and those disclosed in U.S. Pat. Nos. 4,539,996, 4,848,353, 5,012,810 and 5,133,356 are preferred.

In some instances, the biomedical electrical conductor can be an electrically conductive tab extending from the periphery of the biomedical electrodes such as that seen in U.S. Pat. No. 4,848,353 or can be a conductor member extending through a slit or seam in a insulating backing member, such as that seen in U.S. Pat. No. 5,012,810. Alternatively, an electrically conductive tab such as that seen in U.S. Pat. No. 5,012,810 can have an eyelet or other snap-type connector secured thereto.

Automated machinery can be employed to make electrodes 10 and 40. One skilled in the art of making electrodes can select from a variety of machinery manufacturers and manufacturing techniques to minimize manufacturing expense and waste. Some types of machinery are disclosed in U.S. Pat. Nos. 4,715,382 (Strand); 5,133,356 (Bryan et al.); and copending, coassigned U.S. patent application Ser. No. 08/343,353 (Kantner et al.), the disclosures of which are incorporated by reference herein. Another method of manufacturing biomedical electrodes is disclosed in U.S. Pat. No. 5,352,315 (Carrier et al.).

Further embodiments are disclosed in the following examples.

EXAMPLES

Example 1

A number of inks with the different conductive carbon and graphite powders were made. Table-1 shows the formulae of these conductive inks. These inks were prepared by sand mill for 2 to 24 hours after premixing for 10 to 30 minutes of raw materials by high shear mixer. These inks were used for blend inks with Ag or Ag/AgCl ink.

TABLE-1

Formulae of coating inks

| | Graphite Ink | | High conductive carbon ink | | | |
|---|---|---|---|---|---|---|
| | -M- | -ML- | EC4SB | EC4SP | EC4SBMS | EC4SP2 |
| S-CP Graphite | 7.9 wt. % | 9.9 | — | — | — | — |
| Ketjen Black EC | 2.0 wt. % | — | 4.7 | 4.7 | 5.2 | 5.2 |
| 15% Estane 5703 solution | — | — | — | — | 64.2 | 64.2 |
| 30% Estane 5703 Solution | 40.3 wt % | 40.3 wt % | 29.0 | 29.0 | — | — |
| MEK | — | — | 19.4 | 19.4 | — | — |
| PGMA | 49.8 wt. % | 49.8 wt % | — | 46.9 | 10.8 | 30.6 |
| BCA | — | — | 46.9 | — | 19.8 | — |
| Solids Content (wt. %) | 22.0 wt. % | 22.0 wt % | 13.4 | 13.4 | 14.8 | 14.8 |
| Application | Low porous carbon-containing coating 4 with a BET Method unit square of less than 5 $m^2/m^2$ | | High porous carbon-containing coating 6 with a BET Method unit square of over 40 $m^2/m^2$ | | | |

"S-CP graphite" powder of Nippon Kouen Ind. Co. with surface adsorbing area of about 20 $m^2/g$ using the BET Method
"Ketjen Black EC" carbon black powder of Akzo Co- S-CP with surface adsorbing area of about 950 $m^2/g$ using the BET Method
ESTANE 5703 polyurethane resin of Union Carbide Co. (Tg = −20° C.)
Estane solution: Solvent was the mixture of MEK and Toluene (MEK: Toluene-4:1)
MEK: Methyl Ethyl Ketone (b.p.: 79.6° C.)
Toluene (b.p.: 110.6° C.)
PGMEA: Propylene Glycol mono Methyl Ether Acetate (b.p.: 140° C.)
BCA: Buthyl Carbitol Acetate (b.p.: 246.8° C.)

Example 2

Several blend inks with graphite ink -M- and commercialized R-301 solvent-based Ag/AgCl ink(Solids Content: 55.6 wt.%) of ERCON Inc., and blend inks with high conductive carbon ink EC4SB and commercialized R-301 solvent based Ag/AgCl ink of ERCON Inc., were prepared by mixing with polyisocyanate PAPI 135 of Dow Mitsubishi Kasei Co. as the crosslinking agent. The mixing ratio was 0.3 to 0.5 weight percent of crosslinking agent for the inks.

The inks were then coated on 75 μm polyester film of EMBLET T-75 of UNITTKA Co. by hand spread with 100 μm gap distance and dried for 5 minutes under 100° C. to 160° C. The adsorbing surface area of the low porous carbon-containing coating was a unit square of about 4 to 5 $m^2/m^2$. The adsorbing surface area of the high porous carbon-containing coating was a unit square of about 40 to 60 $m^2/m^2$. The coatings were evaluated for dried coating thickness, surface resistance, adhesion strength on base film, toughness for vending and pencil hardness. Adhesion strength was evaluated by seeing if the coatings delaminated from non-conductive film by peeling of a strip of Scotch brand tape #810 (3M Company of St. Paul, Minn., USA), after the strip of #810 tape was adhered on the coating 4. The toughness was evaluated by seeing if the coating delaminated by 5 times bending into a hair pin shape.

Table-2 and Table-3 show the performances of several single coatings. The dried coated thicknesses ranged from 13 to 20 μm.

The surface resistance of coatings with inks shown in Table-2 were about 80 to 110 ohms/sq. and did not depend on the amount of Ag/AgCl ink present in the coating.

On the other hand, the surface resistance of coatings with inks shown in Table-3 were larger than for coatings with inks shown in Table-2 because the loading of conductive carbon powder in coating with inks shown in Table 3 was smaller than the loading of graphite powder in coating with ink shown in Table-2. The range of surface resistance for coatings with inks shown in Table-3 were 120 to 180 ohms/sq. and depended on the amount of Ag/AgCl ink present in coating with ink shown in Table-3. Distribution of Ag/AgCl particles in coating with ink shown in Table 2 seemed different from the distribution of Ag/AgCl particles in coating with ink shown in Table-3. The factor which controlled surface resistance of coating with ink shown in Table-2 was graphite particles, whereas the factor which controlled surface resistance was for coating with ink shown in Table-3 was Ag/AgCl particles. The adhesion strength of those coatings on the polyester base film and the toughness by bending of all coated sheets were acceptable for use.

TABLE-2

Physical performance of Low Porous Carbon-containing Coatings (Graphite-M- ink, R-301 Ag/AgCl ink and PAPI 135 polyisocyanate)

| Sample Number | 1 | 2 | 3 | 4 | 5 | 6 | 7 | 8 | 9 |
|---|---|---|---|---|---|---|---|---|---|
| Graphite ink (Wt. %) | 100 | 98 | 96 | 94 | 92 | 90 | 88 | 80 | 0 |
| Ag/AgCl ink (Wt. %) | 0 | 2 | 4 | 6 | 8 | 10 | 12 | 20 | 100 |
| Solid Graphite ink (Wt. %) | 100 | 95 | 90 | 85 | 80 | 75 | 70 | 50 | 0 |
| Solid Ag/AgCl ink (Wt. %) | 0 | 5 | 10 | 15 | 20 | 25 | 30 | 50 | 100 |
| Thickness ($\mu$m) | 14 | 15 | 15 | 15 | 13 | 15 | 14 | 14 | 20 |
| Surface Resistance Ω/sq. | 82 | 82 | 96 | 96 | 103 | 96 | 96 | 103 | 0.3 |
| Adhesion test on base film | OK | OK | OK | OK | OK | OK | OK | OK | FAIR |
| Toughness test | OK | OK | OK | OK | OK | OK | OK | OK | OK |

TABLE-3

Physical performance of High Porous Carbon-containing Coatings (High conductive carbon ink EC4SB, R-301 Ag/AgCl ink and PAPI 135 polyisocyanate)

| Sample Number | 1 | 2 | 3 | 4 | 5 | 6 |
|---|---|---|---|---|---|---|
| Carbon ink (Wt. %) | 100 | 98 | 96 | 94 | 92 | 90 |
| Ag/AgCl ink (Wt. %) | 0 | 2 | 4 | 6 | 8 | 10 |
| Solid Carbon ink (Wt. %) | 100 | 92 | 84 | 76 | 68 | 60 |
| Solid Ag/AgCl ink (Wt. %) | 0 | 8 | 16 | 24 | 32 | 40 |
| Thickness ($\mu$m) | 14 | 13 | 15 | 14 | 14 | 15 |
| Surface Resistance Ω/sq. | 178 | 178 | 148 | 150 | 137 | 123 |
| Adhesion test on base film | OK | OK | OK | OK | OK | OK |
| Toughness test | OK | OK | OK | OK | OK | OK |

Example 3

The electrical conductors described in Example 2 were laminated with a conductive (produced according to Example 7 of U.S. Pat. No. 4,848,353 and having the following ingredients with the following weight percents: acrylic acid (9.5); N-vinyl-2-pyrrolidone (9.5); glycerin (51.58); water (25.5); benzildimethylketal (0.7); triethylene glycol bismethacrylate (0.09); potassium chloride (1.0); NaOH (2.64); and guar gum (0.12)) on one part of the coating to make biomedical electrodes in the form of electrode as seen in FIG. 2. Electrodes were cut from the laminated sheet. The cut electrode consisted of pad portion 18 of conductive adhesive with dimensions of 2.03 cm×2.54 cm and tab portion 20 without conductive adhesive with dimensions of 2.03 cm×1.01 cm.

The initial electrical performance of electrodes were evaluated according to AAMI (Association for the Advancement of Medical Instrumentation) standards for disposable ECG Electrodes. The measured items were DC offset after 60 seconds, AC impedance at 10 Hz, Simulated Defibrillation Recovery(SDR) after 5 seconds and the highest slope of SDR for 4th pulse. The specification standards mandated by AAMI are shown in Table-4.

Table-5 and 6 showed the initial performance under AAMI standards for the electrodes. The electrodes with coatings with inks shown in Table-2 had to have at least about 25 weight percent of Ag/AgCl ink in coating with ink shown in Table 2 in order to satisfy AAMI standards. Without Ag/AgCl ink, AC impedance was too large and a conductor made from coatings with ink shown in Table-2 without such Ag/AgCl ink would not be suitable for use in a biomedical electrode. Because coating with ink shown in Table-2 did not absorb much water and surface area of graphite particles in the coating shown in Table 2 were small, only Ag/AgCl particles on the surface reacted with electrolyte from the conductive adhesive. Also surface area for an electrochemical reaction in coating with ink shown in Table-2 was insufficient, causing AC impedance to be about 1900 ohms. The optional Ag/AgCl ink was added to improve performance.

The electrodes with coatings with inks shown in Table-3 satisfied AAMI standards with 16 weight percent of Ag/AgCl ink in coating. AC impedance results were excellent. Because coating with ink shown in Table-3 absorbed water and because the surface area of carbon particles was large, Ag/AgCl particles within the coating could react the electrolyte from the conductive adhesive. The overall surface area for an electrochemical reaction in coating with ink in Table-3 was sufficient, causing AC impedance to be about 300 ohms. The use of Ag/AgCl ink in small quantities in coating with ink shown in Table-3 satisfies AAMI standards.

TABLE-4

| AAMI Standards | |
|---|---|
| DC Offset: | Less than 100 mV |
| AC Impedance: | Less than 2000 ohms |
| SDR: | Less than 100 mV |
| SLOPE: | Absolute value is less than 1.0 mV/s |

TABLE-5

AAMI Performance of Electrodes Having Low Porous Carbon-containing Coating From Example 2

| Sample Number | 1 | 2 | 3 | 4 | 5 | 6 | 7 | 8 |
|---|---|---|---|---|---|---|---|---|
| Graphite ink (Wt. %) | 100 | 98 | 96 | 94 | 92 | 90 | 88 | 80 |
| Ag/AgCl ink (Wt. %) | 0 | 2 | 4 | 6 | 8 | 10 | 12 | 20 |
| Solid Graphite | 100 | 95 | 90 | 85 | 80 | 75 | 70 | 50 |
| Solid Ag/AgCl ink (Wt. %) | 0 | 5 | 10 | 15 | 20 | 25 | 30 | 50 |
| Thickness (μm) | 14 | 15 | 15 | 15 | 13 | 15 | 14 | 14 |
| DCO (mV) | 48.6 | −6.4 | −41.2 | −0.8 | 0.6 | −2.7 | −0.5 | −2.6 |
| ACZ (Ω) | Over | 2506 | 2508 | 2220 | 1949 | 1952 | 1713 | 1747 |
| SDR (mV) | Over | Over | 57.2 | 54.3 | 46.4 | 43.5 | 8.9 | 35.6 |
| SLOPE (mV/s) | Over | Over | −1.7 | −1.3 | −1.0 | −0.8 | −0.5 | −0.6 |

DCO: DC offset
ACZ: AC impedance at 10 Hz
SDR: Simulated Defibrillation Recovery
SLOPE: Highest slope at 5 second of 4th pulse

TABLE-6

AAMI Performance of Electrodes with High Porous Carbon-containing Coating From Example 2

| Sample | 1 | 2 | 3 | 4 | 5 | 6 |
|---|---|---|---|---|---|---|
| Carbon ink (Wt. %) | 100 | 98 | 96 | 94 | 92 | 90 |
| Ag/AgCl ink (Wt. %) | 0 | 2 | 4 | 6 | 8 | 10 |
| Solid carbon ink (Wt. %) | 100 | 92 | 84 | 76 | 68 | 60 |
| Solid Ag/AgCl ink (Wt. %) | 0 | 8 | 16 | 24 | 32 | 40 |
| Thickness (μm) | 14 | 13 | 15 | 14 | 14 | 15 |
| DCO (mV) | −63.3 | −1.4 | −1.7 | −0.1 | −0.2 | 0.5 |
| ACZ (Ω) | 430 | 350 | 348 | 300 | 289 | 284 |
| SDR (mV) | Over | 32.1 | 19.9 | 18.4 | 8.2 | 22.6 |
| SLOPE (mV/s) | Over | −1.2 | −0.6 | −0.5 | −0.4 | −0.4 |

Example 4

A high conductive carbon ink EC4SP from Example 1 with low boiling point solvents for quick drying was made. The blend ink of EC4SP and R-301 Ag/AgCl ink of ERCON Inc. and PAPI 135 polyisocyanate crosslinking agent from Example 2 was coated on 75 μm polyester film by hand spread, and dried under 110° C. for 5 minutes. The thickness of the dried conductor was 10 μm, and the adsorbing surface area was about 60 $m^2/m^2$. The ink formula is shown in Table-7.

The coated sheet was laminated with the same conductive adhesive as in Example 3 to make biomedical electrodes 10 of the same size as in Example 3. Even though AC impedance was about 400 ohms, initial electrical performance of the electrodes satisfied AAMI standards. However, the performance of the electrodes after 1 week at 75° C. was poor with failure of the AAMI standard for slope and discoloration of conductive adhesive. Table-8 shows the performance of these degraded electrodes. AC impedance depended on the structure of the coatings within ink shown in Table-7. Coating with ink shown in Table-7 was a porous structure caused by flash evaporation of low boiling point solvent or coagulation of binder causing an unacceptable surface resistance for the coating. Because Ketjen Black EC carbon black powder has a large absorbing surface area, electrolyte like water and salt, and glycerin diffused through the pores and grain gaps in coating, and local electrochemical cells in the coating were formed. The local cells seemed to interfere with charge transfer between ions and electron, causing degradation of highest slope values.

TABLE-7

| Formula of Ink | |
|---|---|
| EC-4SP carbon ink | 91.5 wt. % |
| R -301 Ag/AgCl ink | 8.0 wt. % |
| PAPI 135 polyisocyanate | 0.5 wt. % |

TABLE-8

AAMI Test For Ink Formula of TABLE-7

| | DCO (mV) | ACZ (Ω) | SDR (mV) | SLOPE (mV/s) |
|---|---|---|---|---|
| Initial | 1.0 | 424 | 38.3 | −0.6 |
| 1 week | 0.6 | 480 | 38.3 | −1.2 |

Example 5

In order to inhibit the degradation of the highest slope of SDR seen in Example 4 and reduce the amount of costly Ag/AgCl ink in biomedical electrodes, an electrical conductor comprising a variety of coating formulations was prepared the film of Example 4. The inks used for coating was EC4SP2 carbon ink, Graphite -M-; and the Ag/AgCl ink was R-301 Ercon ink. Crosslinking agent PAPI 135 polyisocyanate of about 0.5 weight percent was used in blended inks.

After mixing, the various inks were coated on a 75 μm thick polyester film and dried at 160° C. for 5 minutes to make electrical conductors having a dried thickness of about 10 μm. The solids content of Ag/AgCl in the coating was about 13 to 19 weight percent.

Biomedical electrodes were made according to Example 3 above and evaluated for AAMI standards. Table-9 below shows the total absorbing surface area of the powders as measured by the BET Method, the unit square of adsorbing surface area as measured by the BET Method, and AAMI results.

TABLE-9

AAMI Performance of Electrodes From Example 5

| Sample Number | A | B | C | D | E |
|---|---|---|---|---|---|
| EC4SP2 Carbon Iink (Wt. %) | 93.5 | 84.1 | 65.5 | 37.4 | 0 |
| Graphite -M- ink (Wt. %) | 0 | 9.4 | 28.0 | 56.1 | 93.5 |

TABLE-9-continued

AAMI Performance of Electrodes From Example 5

| Sample Number | A | B | C | D | E |
|---|---|---|---|---|---|
| R-301 Ag/AgCl ink (Wt. %) | 6 | 6 | 6 | 6 | 6 |
| PAPI 135 (Wt. %) | 0.5 | 0.5 | 0.5 | 0.5 | 0.5 |
| Solid carbon ink (Wt. %) | 78.4 | 67.8 | 49.3 | 25.5 | 0 |
| Solid Graphite -M- ink (Wt. %) | 0 | 11.3 | 31.3 | 56.8 | 84.3 |
| Solid Ag/AgCl ink (Wt. %) | 18.8 | 18.2 | 16.9 | 15.4 | 13.7 |
| Solid PAPI (Wt. %) | 2.8 | 2.7 | 2.5 | 2.3 | 2.0 |
| Thickness ($\mu$m) | 10 | 10 | 10 | 10 | 10 |
| Absorbing Surface Area of carbon powders ($m^2/g$) | 950 | 820 | 617 | 400 | 208 |
| Absorbing Surface Area of Unit Square of Coating ($m^2/m^2$) | 58.9 | 45.2 | 8.2 | 4.3 | — |
| DCO (mV) | −0.5 | −0.8 | 0.1 | 0.4 | 0.2 |
| ACZ (Ω) | 465 | 412 | 546 | 2262 | >3000 |
| SDR (mV) | 22.2 | 22.9 | 27.3 | 45.8 | 72.0 |
| SLOPE (mV/s) | −0.5 | −0.5 | −0.9 | −1.9 | −3.5 |

Sufficient initial AAMI performance was achieved when the unit square surface area for the coating was greater than 8 $m^2/m^2$, thereby qualifying Samples A and B. Diffusion of electrolyte into the coatings of Samples D and E. was quite limited and limited acceptable electrochemical performance. Sample C was marginal in the Slope result.

An aging test was carried with Samples A–E in order to evaluate the stability of these electrodes prepared in this Example 5. The electrodes were put into a moisture barrier pouch, and the pouch was sealed by heat sealer. The pouch was stored in oven of 57° C. for a maximum of 10 weeks, with intermediate testing at 3, 5, and 8 weeks. After aging for each period, the pouch was removed and cooled to room temperature, and opened. The aged electrodes were evaluated against AAMI standards. The electrodes satisfied AAMI standards. This accelerated aging study computes to a shelf life of about two years with storage at about 24 to 25° C. according to the Von't Hoff relationship known to those skilled in the art.

Table-10 shows the performance for aged electrodes after aging for initial, 3, 5, 8 and 10 weeks.

TABLE-10

AAMI Performance of Electrodes From Comparison Example 5 After Aging at 57° C.

| Sample Number | A | B | C | D | E |
|---|---|---|---|---|---|
| AAMI Testing Initial | OK | OK | Fair | Not Good | Not Good |
| 3 Weeks | OK | OK | Fair | — | — |
| 5 Weeks | OK | OK | Fair | — | — |
| 8 Weeks | OK | OK | Not Good | — | — |
| 10 Weeks | Not Good | Not Good | — | — | — |

Both Samples A and B performed adequately through 8 weeks, but none of the Samples lasted the entire aging term of ten weeks. A single coating of a high porous carbon-containing coating diffuses too much electrolyte and fails to maintain stability for acceptable aging terms. A thicker coating could improve performance but would add unacceptable cost to the manufacture of the electrode.

Example 6

By contrast to Example 4 and Example 5, Example 6 tested a film with dual coatings, several low porous carbon-containing coatings on the film and the highest porous carbon-containing coating on several low porous carbon-containing coatings to keep enough aging stability. The thickness of the high porous carbon-containing coating was 5 $\mu$m and the thickness of the several low porous carbon-containing coating was also 5 $\mu$m and had a solids content of Ag/AgCl ink of 2.4 to 3.6 weight percent. Table-11 shows the ink formulations and the AAMI results.

The electrodes were prepared in the same manner as in Example 3, except for the formulations and the structure of the electrode. The base ink used for coating 4 was Graphite -M-; the carbon black ink was EC4SP2; and the Ag/AgCl ink was R-301 Ercon ink. Crosslinking agent PAPI 135 polyisocyanate of about 0.5 weight percent was used in the total ink.

TABLE 11

AAMI Performance of Electrodes From Example 6

| Sample Number | Sample Number | F | G | H | I | J | K | L |
|---|---|---|---|---|---|---|---|---|
| Top Coating | EC4SP2 Carbon ink (Wt. %) | 93.5 | 93.5 | 93.5 | 93.5 | 93.5 | 93.5 | 93.5 |
| | R-301 Ag/AgCl ink (Wt. %) | 6.0 | 6.0 | 6.0 | 6.0 | 6.0 | 6.0 | 6.0 |
| | PAPI 135 (Wt. %) | 0.5 | 0.5 | 0.5 | 0.5 | 0.5 | 0.5 | 0.5 |
| | Solid EC4SP2 ink (Wt. %) | 78.4 | 78.4 | 78.4 | 78.4 | 78.4 | 78.4 | 78.4 |
| | Solid Ag/AgCl ink (Wt. %) | 18.8 | 18.8 | 18.8 | 18.8 | 18.8 | 18.8 | 18.8 |
| | Solid PAPI (Wt. %) | 2.8 | 2.8 | 2.8 | 2.8 | 2.8 | 2.8 | 2.8 |
| | Thickness ($\mu$m) | 5 $\mu$m | 5 $\mu$m | 5 $\mu$m | 5 $\mu$m | 5 $\mu$m | 5 $\mu$m | 5 $\mu$m |
| Base Coating | EC4SP2 Carbon ink (Wt. %) | 98.5 | 88.7 | 78.8 | 39.4 | — | — | 19.7 |
| | Graphite -M- ink (Wt. %) | — | 9.8 | 19.7 | 59.1 | 98.5 | — | — |
| | Graphite -ML- ink (Wt. %) | — | — | — | — | — | 98.5 | 78.8 |
| | R-301 Ag/AgCl ink (Wt. %) | 1.0 | 1.0 | 1.0 | 1.0 | 1.0 | 1.0 | 1.0 |
| | PAPI 135 (Wt. %) | 0.5 | 0.5 | 0.5 | 0.5 | 0.5 | 0.5 | 0.5 |
| | Solid EC4SP2 ink (Wt. %) | 93.2 | 80.5 | 68.5 | 29.3 | — | — | 13.7 |
| | Solid Graphite -M- ink (Wt. %) | — | 13.2 | 25.4 | 65.4 | 95.4 | — | — |
| | Solid Graphite -ML- ink (Wt. %) | — | — | — | — | — | 95.4 | 81.4 |
| | Solid Ag/AgCl ink (Wt. %) | 3.6 | 3.4 | 3.2 | 2.8 | 2.4 | 2.4 | 2.6 |
| | Solid PAPI (Wt. %) | 3.2 | 2.9 | 2.9 | 2.5 | 2.2 | 2.2 | 2.3 |
| | Thickness ($\mu$m) | 5 $\mu$m | 5 $\mu$m | 5 $\mu$m | 5 $\mu$m | 5 $\mu$m | 5 $\mu$m | 5 $\mu$m |
| | Absorbing Surface Area of Carbon Powders ($m^2/g$) | 950 | 820 | 617 | 400 | 208 | 20 | 128 |

TABLE 11-continued

AAMI Performance of Electrodes From Example 6

| Sample Number | Sample Number | F | G | H | I | J | K | L |
|---|---|---|---|---|---|---|---|---|
| | Absorbing Surface Area of Unit Square of Coating $m^2/m^2$ | — | 26.9 | 5.5 | 4.4 | 4.8 | 3.1 | — |
| AAMI performance of electrodes | DCO (mV) | −0.7 | −0.3 | 0.2 | −0.4 | 0.0 | −1.0 | 1.2 |
| | ACZ (Ω) | 434 | 380 | 356 | 324 | 469 | 1635 | 1513 |
| | SDR (mV) | 22.6 | 23.8 | 22.5 | 22.3 | 23.8 | 24.5 | 24.7 |
| | SLOPE (mV/s) | −0.5 | −0.5 | −0.5 | −0.4 | −0.6 | −0.6 | −0.7 |

Samples F–L showed acceptable results. But Samples K and L showed a little higher AC impedance by high resistance of base conductive layer with lower porous structure.

Aging studies were also conducted on Samples F–L in the same manner as in Comparison Example 5. Table-12 shows the results.

TABLE-12

AAMI Performance of Electrodes From Example 6 After Aging at 57° C.

| Sample Number | F | G | H | I | J | K | L |
|---|---|---|---|---|---|---|---|
| AAMI Testing Initial | Good | Good | Good | Good | Good | Fair | Fair |
| 3 Weeks | Good | Good | Good | Good | Good | Fair | Fair |
| 5 Weeks | Good | Good | Good | Good | Good | Fair | Fair |
| 8 Weeks | Not Good | Not Good | Not Good | Good | Good | Fair | Fair |
| 10 Weeks | — | — | — | Good | Good | Fair | Fair |

Samples I–L showed acceptable results, and Samples F–H showed unacceptable results. As samples F–H have porous base layer, the electrolyte could be diffused into the base layer.

When considering the combination of initial and aged AAMI performance results, Samples I and J are preferred for use in biomedical electrodes of the present invention to keep good performance.

Example 7

In order to reduce the amount of costly Ag/AgCl ink in biomedical electrodes with sample J of Example 6, an electrical conductor comprising dual coatings 4 without Ag/AgCl ink and 6 was prepared on film 2. The base ink used for coating 4 was Graphite -M-. The top ink used for coating 6 was the carbon ink EC4SP2; and the Ag/AgCl ink was R-301 Ercon ink. Crosslinking agent PAPI 135 polyisocyanate of about 0.5 weight percent was used in the total ink. The conductor used film 2 having a 5 μm coating 4 and a 5 μm coating 6, coated by a tandem method with the following parameters: Speed: 2 m/m, drying for base layer: 110° C. for 105 sec.; and for top layer: 160° C. for 105 sec.

The performance showed acceptable results. But, AC impedance of the electrodes were a little high.

TABLE-13

Initial AAMI Performance of Electrodes From Example 7

| | Sample Number | M | N |
|---|---|---|---|
| Top Coating | EC4SP2 Carbon Ink (Wt. %) | 93.5 | 91.5 |
| | R-301 Ag/AgCl ink (Wt. %) | 6.0 | 8.0 |

TABLE-13-continued

Initial AAMI Performance of Electrodes From Example 7

| | Sample Number | M | N |
|---|---|---|---|
| | PAPI 135 (Wt. %) | 0.5 | 0.5 |
| | Solid carbon ink (Wt. %) | 78.3 | 73.2 |
| | Solid Ag/AgCl ink (Wt. %) | 18.9 | 24.1 |
| | Solid PAPI (Wt. %) | 2.8 | 2.7 |
| | Thickness (μm) | 5 | 5 |
| Base coating | Graphite -M- ink (wt. %) | 99.5 | 99.5 |
| | PAPI 135 (Wt. %) | 0.5 | 0.5 |
| | Solid Graphite-M-ink (Wt. %) | 97.8 | 97.8 |
| | Solid PAPI 135 (Wt. %) | 2.2 | 2.2 |
| | Thickness (μm) | 5 | 5 |
| | Absorbing Surface Area of carbon powders ($m^2/g$) | 208 | 208 |
| | Absorbing Surface Area of Unit Square of Coating $m^2/m^2$ | 4.8 | 4.8 |
| AAMI performance of electrodes | DCO (mV) | 0.6 | 0.5 |
| | ACZ (Ohms) | 410 | 493 |
| | SDR (mV) | 22.6 | 22.8 |
| | SLOPE(mV/s) | −0.5 | −0.4 |

Example 8

In order to get lower AC impedance, the experiment of Example 7 was repeated, except for the base low porous carbon-containing coating 4 being 10 μm thick. The ink used for coating 4 was Graphite -M-. And the top ink for coatings 6 was the carbon black ink was EC4SP2; and the Ag/AgCl ink was R-301 Ercon ink. Crosslinking agent PAPI 135 polyisocyanate of about 0.5 weight percent was used in the total ink. Table-14 shows the results.

TABLE-14

| | Sample Number | O | P |
|---|---|---|---|
| Top Coating | EC4SP2 Carbon Ink (Wt. %) | 93.5 | 91.5 |
| | R-301 Ag/AgCl ink (Wt. %) | 6.0 | 8.0 |
| | PAPI 135 (Wt. %) | 0.5 | 0.5 |
| | Solid carbon ink (Wt. %) | 78.3 | 73.2 |
| | Solid Ag/AgCl ink (Wt. %) | 18.9 | 24.1 |
| | Solid PAPI (Wt. %) | 2.8 | 2.7 |
| | Thickness (μm) | 5 | 5 |
| Base coating | Graphite -M- ink (wt. %) | 99.5 | 99.5 |
| | PAPI 135 (Wt. %) | 0.5 | 0.5 |
| | Solid Graphite-M-ink (Wt. %) | 97.8 | 97.8 |
| | Solid PAPI 135 (Wt. %) | 2.2 | 2.2 |
| | Thickness (μm) | 10 | 10 |
| | Absorbing Surface Area of carbon powders ($m^2/g$) | 208 | 208 |
| | Absorbing Surface Area of Unit Square of Coating $m^2/m^2$ | 4.5 | 4.5 |
| AAMI performance of electrodes | DCO (mV) | −0.1 | 0.2 |
| | ACZ (Ohms) | 342 | 357 |

TABLE-14-continued

| Sample Number | O | P |
|---|---|---|
| SDR (mV) | 23.3 | 23.2 |
| SLOPE (mV/s) | −0.4 | −0.4 |

Example 9

Surface hardness of the electrical conductor was tested to assure that the conductor could withstand mechanical wear with an electrical connector electrically connected to biomedical instrumentation. The surface hardness test is described as follows: Several kinds of pencils, which hardness is 2B, B, HB, H, 2H, 3H and 4H, were prepared. Straight lines were written by each pencil. The pencil hardness was determined the lowest softness (hardness) not to make scratches.

Dual coatings 4 and 6 cover pad portion 20 but coating 6 need not cover tab portion 18 of electrode 10, to save some cost of manufacture. Thus, coating 4 needs sufficient thickness to withstand mechanical wear at tab portion 18 while also providing sufficient electrical connection to biomedical instrumentation.

The experiment tested surface hardness of both coatings 4 and 6 and AAMI performance standards, where coating 4 cover all of film 2 and where coating 6 covered only pad portion 20. The base ink used for coating 4 was Graphite -M-; and the Ag/AgCl ink was R-301 Ercon ink. The top ink used for coating 6 was EC4SP2 carbon ink; the Ag/AgCl ink was R301 Ercon ink. Crosslinking agent PAPI 135 polyisocyanate of about 0.5 weight percent was used in the total ink. Table 15 shows the results.

TABLE-15

Physical and AAMI Performance of Electrodes From Example 9

| | Sample Number | Q | R |
|---|---|---|---|
| Top Coating | EC4SP2 Carbon Ink (Wt. %) | 93.5 | 93.5 |
| | R-301 Ag/AgCl ink (Wt. %) | 6.0 | 6.0 |
| | PAPI 135 (Wt. %) | 0.5 | 0.5 |
| | Solid carbon ink (Wt. %) | 73.2 | 73.2 |
| | Solid Ag/AgCl ink (Wt. %) | 24.1 | 24.1 |
| | Solid PAPI (Wt. %) | 2.7 | 2.7 |
| | Thickness ($\mu$m) | 5 | 5 |
| Base coating | Graphite -M- ink (wt. %) | 99.5 | 98.5 |
| | R-301 Ag/AgCl ink (Wt. %) | 0.0 | 1.0 |
| | PAPI 135 (Wt. %) | 0.5 | 0.5 |
| | Solid Graphite-M-ink (Wt. %) | 97.8 | 95.4 |
| | Solid Ag/AgCl ink (Wt. %) | 0.0 | 2.4 |
| | Solid PAPI 135 (Wt. %) | 2.2 | 2.2 |
| | Thickness ($\mu$m) | 13 | 10 |
| | Absorbing Surface Area of carbon powders $m^2/g$ | 208 | 208 |
| | Absorbing Surface Area of Unit Square of Coating $m^2/m^2$ | 4.8 | 4.3 |
| AAMI performance of electrodes | DCO (mV) | 0.6 | 0.5 |
| | ACZ (Ohms) | 410 | 493 |
| | SDR (mV) | 22.6 | 22.8 |
| | SLOPE (mV/s) | −0.5 | −0.4 |
| Surface Resistance (Ω/sq.) | Top Layer 6 | 27 | 55 |
| | Bottom Layer 4 | 48 | 96 |
| Surface Hardness (Pencil Hardness) | Top Layer 6 | H | H |
| | Base Layer 4 | 3H | 3H |
| AAMI performance of electrodes (repeated) | DCO (mV) | −0.3 | −0.4 |
| | ACZ (Ohms) | 203 | 352 |
| | SDR (mV) | 24.5 | 24.6 |
| | SLOPE (mV/s) | −0.4 | −0.4 |

As graphite is harder than carbon black, the surface hardness of the graphite coating is harder than the carbon black coating.

Both physical and AAMI electrical properties of electrical conductor samples Q and R are excellent for use in biomedical electrodes of the present invention.

The invention is not limited to the embodiments disclosed. The claims follow.

What is claimed is:

1. A biomedical electrode, comprising an electrical conductor and an ionically conductive medium containing an electrolyte in contact with the electrical conductor, wherein the electrical conductor comprises a flexible, non-conductive film and two different carbon-containing coatings on a major surface of the film, wherein one carbon-coating coating is a low porous carbon-containing coating having an $N_2$ adsorbing surface area of less than about 5 $m^2/m^2$ of unit area and wherein one carbon-coating coating is a high porous carbon-containing coating having an $N_2$ adsorbing surface area of more than about 8 $m^2/m^2$ of the unit area.

2. The biomedical electrode of claim 1, wherein the low porous carbon-containing coating contacts the film, wherein the high porous carbon-containing coating contacts the low porous carbon-containing coating, and wherein the electrolyte diffuses into the high porous carbon-containing coating.

3. The biomedical electrode of claim 2, wherein the low porous carbon-containing coating comprises carbon powder and hydrophobic polymeric binder, optionally silver-containing powder, and optionally crosslinking agent, and wherein the high porous carbon-containing coating comprises silver-containing powder, carbon powder, a hydrophobic or hydrophilic polymeric binder, and optionally a crosslinking agent.

4. The biomedical electrode of claim 2, wherein at least a part of an end of the high porous carbon-containing coating forming a tab area is not covered with the ionically conductive medium.

5. The biomedical electrode of claim 2, wherein at least a part of an end of the low porous carbon-containing coating forming a tab area is not covered with any of the high porous carbon-containing coating.

6. The biomedical electrode of claim 1, wherein the low porous carbon-containing coating includes silver-containing powder comprising silver, silver halide, or combinations thereof.

7. The biomedical electrode of claim 3, wherein the hydrophobic polymeric binder has minimal or little water absorbency.

8. The biomedical electrode of claim 1, wherein the flexible, non-conductive film has a thickness from about 1 $\mu$m to about 200 $\mu$m, wherein the low porous carbon-containing coating has a thickness from about 1 to about 20 $\mu$m, and wherein the high porous carbon-containing coating has a thickness from about 1 to about 20 $\mu$m.

9. The electrical conductor of claim 1, wherein the film is selected from the group consisting of polyester, poly(ethylene), poly(propylene), and poly(vinyl chloride).

10. The biomedical electrode of claim 3, wherein the carbon powder for the low porous carbon-containing coating comprises graphite powder, carbon black powder, or combinations thereof, and wherein the carbon powder for the high porous carbon-containing coating comprises graphite powder, carbon black powder, or combinations thereof.

11. The biomedical electrode of claim 3, wherein a total content of silver-containing powder in the high porous carbon-containing coating ranges from about 0.5 to about 30 weight percent;

wherein a content of the hydrophobic or hydrophilic polymeric binder in the high porous carbon-containing coating ranges from about 20 to about 90 weight percent;

wherein a total content of silver-containing powder in the low porous carbon-containing coating is less than about 12 weight percent;

wherein a content of the hydrophobic polymeric binder in the low porous carbon-containing coating ranges from about 30 to about 90 weight percent.

12. The biomedical electrode of claim 11, wherein an average adsorbing surface area of carbon-containing powder in the high porous carbon-containing coating is over about 600 $m^2/g$, and wherein an average diameter of silver-containing powder in the high porous carbon-containing coating ranges from about 0.5 to about 30 $\mu$m, and wherein an average absorbing surface area of carbon-containing powder in the low porous carbon-containing coating is less that 400 $m^2/g$, and wherein an average diameter of silver-containing powder in the low porous carbon-containing coating ranges from about 0.5 to about 30 $\mu$m.

* * * * *